(12) United States Patent
Mitchell et al.

(10) Patent No.: US 8,119,803 B2
(45) Date of Patent: Feb. 21, 2012

(54) PREPARATION OF OPIATE ANALGESICS BY REDUCTIVE ALKYLATION

(75) Inventors: Melville Mitchell, Edinburgh (GB); Neil Kenneth Thomson, West Lothian (GB); George Scott Wilson, Edinburgh (GB); Neil John Goodwin, Edinburgh (GB); Maureen Joan Young, Edinburgh (GB)

(73) Assignee: Johnson Matthey Public Limited Company, London (GB)

( * ) Notice: Subject to any disclaimer, the term of this patent is extended or adjusted under 35 U.S.C. 154(b) by 841 days.

(21) Appl. No.: 11/628,210

(22) PCT Filed: Sep. 14, 2005

(86) PCT No.: PCT/GB2005/003547
§ 371 (c)(1),
(2), (4) Date: Oct. 5, 2007

(87) PCT Pub. No.: WO2006/035195
PCT Pub. Date: Apr. 6, 2006

(65) Prior Publication Data
US 2008/0045715 A1 Feb. 21, 2008

(30) Foreign Application Priority Data
Sep. 30, 2004 (GB) .................................. 0421687.5

(51) Int. Cl.
C07D 489/02 (2006.01)
C07D 489/08 (2006.01)
(52) U.S. Cl. ............................................ 546/45; 546/44
(58) Field of Classification Search ............... 546/45, 546/44, 39, 74
See application file for complete search history.

(56) References Cited

U.S. PATENT DOCUMENTS

| 3,332,950 A | 7/1967 | Blumberg et al. |
| 3,717,643 A | 2/1973 | Archer |
| 3,793,329 A | 2/1974 | Merz et al. |
| 4,082,744 A | 4/1978 | Ikeda et al. |
| 4,190,601 A | 2/1980 | Decker |
| 4,387,097 A | 6/1983 | White |
| 5,869,669 A | 2/1999 | Huang |

FOREIGN PATENT DOCUMENTS
GB 1136214 12/1968

OTHER PUBLICATIONS

Tanaka, H. et al.: Solid-phase synthesis of naltridole derivatives using fischer indole synthesis based on one-pot release and cyclization methodology. Organic Letters, vol. 5, pp. 1159-1162, 2003.*
I. Monković et al., "Total Synthesis and Pharmacological Activities of N-Substituted 3,14-Dihydroxymorphinans,"*Journal of the American Chemical Society*, vol. 95, No. 23, Nov. 14, 1973, pp. 7910-7912.
R. A. Olofson et al., "Selective N-Dealkylation of Tertiary Amines With Vinyl Chloroformate: An Improved Synthesis of Naxolone," *Tetrahedron Letters*, No. 18, 1977, pp. 1567-1570.
Michael P. Kotick et al., "Analgesic Narcotic Antagonists. 8. 7α-epoxymorphinan-6-ones," *Journal of Medicinal Chemistry*, vol. 24, No. 12, 1981, pp. 1445-1450.
Edward R. Atkinson et al., "Emetic Activity of N-Substituted Norapomorphines,"*Journal of Medicinal Chemistry*, vol. 18, No. 10, 1975, pp. 1000-1003.

(Continued)

*Primary Examiner* — Charanjit S Aulakh
(74) *Attorney, Agent, or Firm* — RatnerPrestia

(57) ABSTRACT

A process for preparing a compound of formula (A), (B) or (C):

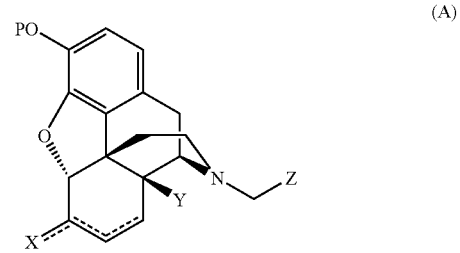

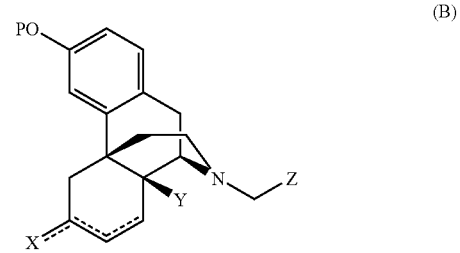

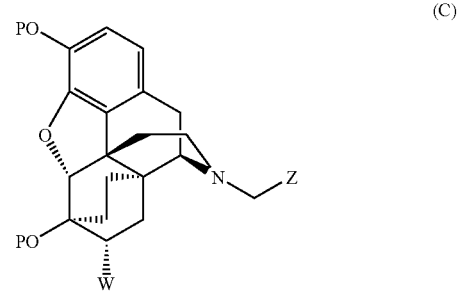

wherein P is H, $CH_3$ or a hydroxyl protecting group; X is O, a protected ketone, OH, a protected hydroxyl group or H; Y is OH, a protected hydroxyl group or H; W is $C(CH_3)_2OH$, $(CH_3)(C(CH_3)_3)OH$ or $COCH_3$; Z is $C_2$-$C_{10}$ alkyl or $C_2$-$C_{10}$ arylalkyl; and ----- is a single bond or a double bond, is disclosed. The process includes reductive alkylation in the presence of hydrogen and a reductive alkylation catalyst.

14 Claims, No Drawings

OTHER PUBLICATIONS

CAplus Abstract Acc. No. 1996:126579.

Helmut Schmidhammer, "Synthesis and Biological Evaluation of 14-Alkoxymorphinans. Part 4: Opioid Agonists and Partial Opioid Agonists in a Series of N-(Cyclobutylmethyl)-14-methoxymorphinan-6-ones," *Helvetica Chimica Acta*, vol. 72, Issue 6, Sep. 20, 1989, pp. 1233-1240.

K. W. Bentley et al., "Novel Analgesics and Molecular Rearrangements in the Morphine-Thebaine Group. III. Alcohols of the 6,14-*endo*-Ethenotetrahydrooripavine Series and Derived Analogs of N-Allylnormorphine and -norcodeine," *Journal of the American Chemical Society*, vol. 89, No. 13, Jun. 21, 1967, pp. 3281-3292.

Johnson et al., "Aldehydes from Acid Chlorides by Reduction of Ester-Mesylates with Sodium Borohydride: Cyclobutanecarboxaldehyde," *Organic Syntheses*, Collective vol. 6, 1988, pp. 312-316.

International Preliminary Report on Patentability dated Nov. 22, 2006.

Notice of Opposition of European Patent dated Jan. 13, 2010.

International Search Report dated Nov. 22, 2005.

Written Opinion of the International Searching Authority dated Nov. 22, 2005.

IUPAC Compendium of Chemical Terminology 2nd Edition (1997) entitled Aryl Groups (1995, 67, 1320) and Heteroaryl Groups (1995, 67, 1340).

"Opponent's Response to the Communication dated Aug. 20, 2010, forwarding a letter from the proprietor of the opposed patent and the Summons to attend oral proceedings pursuant to Rule 115(1) EPC dated Jun. 16, 2011," Filed Sep. 16, 2011, Opposition against European Patent No. 1794165.

Carey et al, "Advanced Organic Chemistry," $3^{rd}$ Edition 1990, p. 219.

March, "Advanced Organic Chemistry: Reactions, Mechanisms & Structure," $4^{th}$ Edition 1992, pp. 771-780.

Morrison et al., "Organic Chemistry," 1959, pp. 629-630.

\* cited by examiner

PREPARATION OF OPIATE ANALGESICS BY REDUCTIVE ALKYLATION

This application is the U.S. National Phase application of PCT International Application No. PCT/GB2005/003547, filed Sep. 14, 2005, and claims priority of British Patent Application No. 0421687.5, filed Sep. 30, 2004.

FIELD OF THE INVENTION

The present invention relates to a process for preparing naltrexone and structurally similar compounds such as nalbuphine, nalmefene, oxilorphan, butorphanol, diprenorphine and buprenorphine. All these compounds contain a cyclic tertiary amine.

BACKGROUND OF THE INVENTION

Naltrexone (1) is a narcotic analgesic:

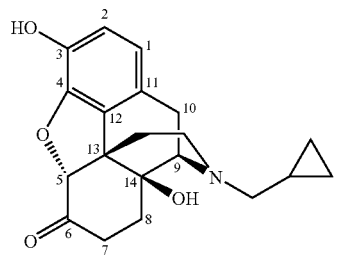
(1)

Nalbuphine (2) and nalmefene (3) are structurally similar compounds:

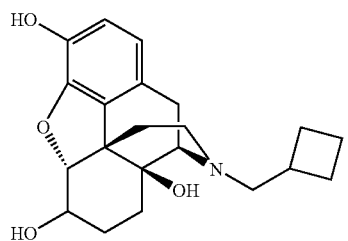
(2)

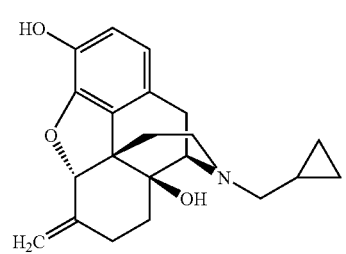
(3)

Oxilorphan (4) and butorphanol (5) are also similar but there is no ether linkage between the so-called A and C rings:

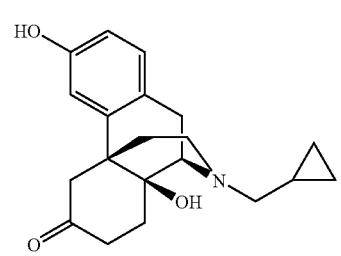
(4)

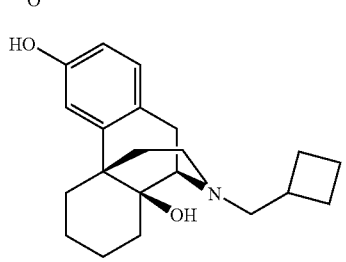
(5)

Diprenorphine (6) and buprenorphine (7) contain an ethyl bridge on the C ring:

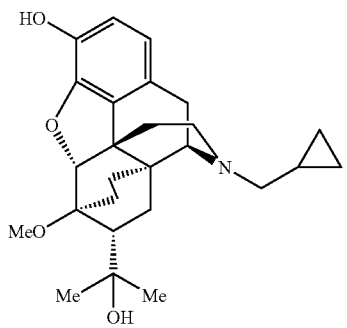
(6)

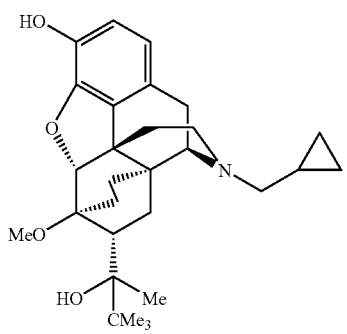
(7)

U.S. Pat. No. 3,332,950 discloses methods for preparing this type of compound. In a first method, Naltrexone is prepared from noroxymorphone in four steps. The method employs a hazardous metal hydride reagent in order to reduce the condensation product formed between a protected noroxymorphone and cyclopropylcarbonyl chloride. In order to prevent side reactions occurring at the ketone functional group, the method incorporates protection and deprotection steps. The inventors believe that this type of process afford yields of approximately 33% naltrexone starting from noroxymorphone hydrochloride. In a second method, naltrexone is prepared by the direct coupling of cyclopropylmethylbromide and noroxymorphone in dimethylformamide. The method employs high temperatures (70° C.) and prolonged reaction times (7 days) yet still only achieves a 60% theoretical yield.

SUMMARY OF THE INVENTION

The present inventors have sought to provide an improved method for preparing naltrexone and similar compounds. Accordingly, the present invention provides a process for preparing a compound of formula (A), (B) or (C):

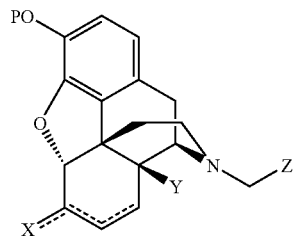
(A)

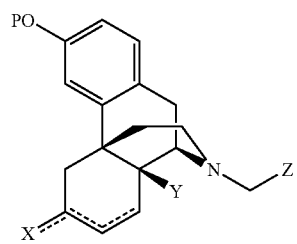
(B)

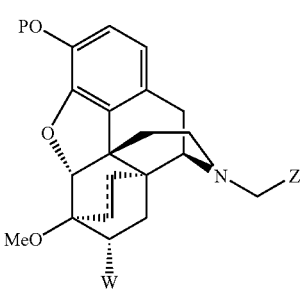
(C)

wherein P is H, $CH_3$ or a hydroxyl protecting group;
X is O, a protected ketone, OH, a protected hydroxyl group or H;
Y is OH, a protected hydroxyl group or H;
W is $C(CH_3)_2OH$, $C(CH_3)(C(CH_3)_3)OH$ or $COCH_3$;
Z is $C_2$-$C_{10}$ alkyl or $C_2$-$C_{10}$ arylalkyl; and ----- is a single bond or a double bond;
wherein a compound of formula (D), (E) or (F):

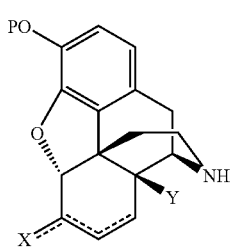
(D)

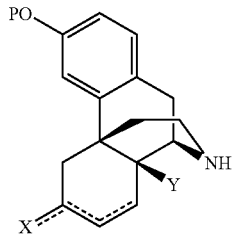
(E)

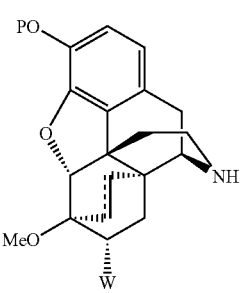
(F)

wherein P, X, Y, W and ----- are as defined above; is reacted with a compound of formula (G):

(G)

wherein Z is as defined above, in the presence of hydrogen and a reductive alkylation catalyst.

DETAILED DESCRIPTION OF THE INVENTION

The method of the invention affords better yields than known processes and avoids the use of hazardous metal hydride reagents that are difficult to handle on a large scale. It does not require high temperatures or prolonged reaction times.

In a preferred embodiment, P is H or $CH_3$, preferably H. In an alternative embodiment, P is a hydroxyl protecting group such as an alkoxy, alkoxycarbonyl, aroxycarbonyl, arylmethyl, silyl ether, carbonate or sulphonate group and is preferably an alkoxy, alkoxycarbonyl, aroxycarbonyl or arylmethyl group. Suitable alkoxycarbonyl groups include propoxycarbonyl and ethoxycarbonyl. Suitable aroxycarbonyl groups include phenoxycarbonyl. Suitable arylmethyl groups include napthylmethyl and benzyl.

X is preferably O (and therefore the bond between X and the $C_6$ ring is a double bond) or OH (and therefore the bond between X and the $C_6$ ring is a single bond). X may be a protected ketone group, e.g. an acetal group. If X is a protected hydroxyl group, the protecting group may be any of the hydroxyl protecting groups as listed above for P.

Y is preferably OH. If Y is a protected hydroxyl group, the protecting group may be any of the hydroxyl protecting groups as listed above for P.

Z is $C_2$-$C_{10}$ alkyl or $C_2$-$C_{10}$ arylalkyl, preferably $C_2$-$C_5$ alkyl. The term "alkyl" includes straight chained, branched, cyclic and substituted alkyls, but preferably the alkyl group is unsubstituted. Preferably, Z is cyclopropyl or cyclobutyl.

The bonds between the 6,7 carbons and the 7,8 carbons in the compounds of formula (A), (B), (D) and (E) may be double bonds or single bonds. Similarly, the bond between the carbons of the ethyl bridge in the compounds of formula (C) and (F) may be a double bond or a single bond. Any double bonds in the compounds of formula (D), (E) or (F) may be hydrogenated in the presence of hydrogen and a reductive alkylation catalyst so compounds of formula (D), (E) and (F) with double bonds may provide compounds of formula (A), (B) and (C) with corresponding single bonds. The skilled person can vary the reaction conditions to favour hydrogenation of double bonds.

In a preferred embodiment of the invention, a compound of formula (D) wherein P is H, X is O and Y is OH, is reacted with a compound of formula (G) wherein Z is cyclopropyl. This provides a compound of formula (A) wherein P is H, X is O, Y is OH and Z is cyclopropyl. If the 6,7 and 7,8 bonds are single bonds, this compound is naltrexone.

In another preferred embodiment of the invention, a compound of formula (D) wherein P is H, X is OH and Y is OH, is reacted with a compound of formula (G) wherein Z is cyclobutyl. This provides a compound of formula (A) wherein P is H, X is OH, Y is OH and Z is cyclobutyl. If the 6,7 and 7,8 bonds are single bonds, this compound is nalbuphine.

In another preferred embodiment of the invention, a compound of formula (E) wherein P is H, X is O and Y is OH or H, is reacted with a compound of formula (G) wherein Z is cyclopropyl. This provides a compound of formula (B) wherein P is H, X is O, Y is OH or H and Z is cyclopropyl. If the 6,7 and 7,8 bonds are single bonds, these compounds are oxilorphan and cyclorphan.

In another preferred embodiment of the invention, a compound of formula (E) wherein P is H, X is H and Y is OH, is reacted with a compound of formula (G) wherein Z is cyclobutyl. This provides a compound of formula (B) wherein P is H, X is H, Y is OH and Z is cyclobutyl. If the 6,7 and 7,8 bonds are single bonds, this compound is butorphanol.

In another preferred embodiment of the invention, a compound of formula (F) wherein P is H and W is $C(CH_3)_2OH$, is reacted with a compound of formula (G) wherein Z is cyclopropyl. This provides a compound of formula (C) wherein P is H, W is $C(CH_3)_2OH$ and Z is cyclopropyl. If the ethyl bridge has a single bond, this compound is diprenorphine.

In another preferred embodiment of the invention, a compound of formula (F) wherein P is H and W is $C(CH_3)(C(CH_3)_3)OH$, is reacted with a compound of formula (G) wherein Z is cyclopropyl. This provides a compound of formula (C) wherein P is H, W is $C(CH_3)(C(CH_3)_3)OH$ and Z is cyclopropyl. If the ethyl bridge has a single bond, this compound is buprenorphine.

Compounds of formula (D), (E), (F) and (G) are known and can be manufactured by a skilled person using known techniques. For example, compounds of formula (D) can be synthesised as described by Olofson et al in Tet. Lett., 1977, pages 1567-70. Compounds of formula (E) can be synthesised as described by Monkovic et al in J. Amer. Chem. Soc., 95, 1973, pages 9710-12. Compounds of formula (F) can be synthesised as described by Bentley et al in J. Amer. Chem. Soc., 89, 1967, 3281-92. Compounds of formula (G) can be synthesised as described in Organic Syntheses, Collective Volume 6, page 312.

Suitable reductive alkylation catalysts are well known to the skilled person and include platinum group metal catalysts (e.g. platinum or palladium), nickel catalysts and mixtures of these catalysts. The amount of catalyst required is suitably 2 mole % or less, preferably about 0.2 mole %. The process is suitably carried out at room temperature or higher, preferably around 50° C. Hydrogen is suitably supplied to the reaction at a pressure of 1 bar or greater, preferably about 3 bar. The solvent is suitably chosen from alcohols, ethers, amines, amides, alkanes, xylenes, chlorinated alkanes or mixtures thereof. A preferred solvent is methanol. The process of the invention may take around 1 or more hours.

Compounds of formula (A), (B) and (C) can be further reacted to provide-useful compounds, e.g. naltrexone produced according to the process of the present invention can be further reacted to provide nalmefene.

EXAMPLES

The following examples are illustrative but not limiting of the invention.

Example 1

Preparation of Naltrexone from Noroxymorphone

To a solution of noroxymorphone (2 g, 6.14 mmol) in methanol (20 ml) was added cyclopropylcarboxaldehyde (0.63 ml, 8.43 mmol). 5% Palladium on carbon catalyst (1 mole % Pd) was added and the mixture was hydrogenated at 50° C. under 3 bar hydrogen pressure for 1 hour. On completion, the catalyst was filtered off and the reaction liquors diluted with chloroform (20 ml) and washed with water (3×20 ml). Evaporation of the solvent yielded naltrexone alkaloid.

Example 2

Preparation of Naltrexone Hydrochloride from Noroxymorphone

Noroxymorphone alkaloid (20.0 g, equivalent to 60.9 mmol dry) was added to a mixture of N-methylpyrrolidinone (60 ml) and methanol (140 ml). Cyclopropanecarboxaldehyde (5.3 ml, 70.9 mmol) and platinum on carbon catalyst were added and the mixture hydrogenated at 40 psi and 50° C. for 1 hour. Upon completion, the catalyst was filtered off and the reaction liquors diluted with chloroform (60 ml) and washed with water (200 ml). The aqueous layer was extracted with chloroform (2×60 ml) and the combined organic layer washed with water (5×140 ml). The organic layer was concentrated down to dryness and the solid residue redissolved in ethanol (100 ml). Hydrochloric acid was added until pH <4.0. The resulting precipitate was filtered, washed with ethanol (10 ml) and dried in oven to yield a white solid. 16.7 g (74% theory). $^1$H NMR ($d_6$-DMSO, δ/ppm): 0.60 (1H, m), 0.70 (1H, m), 0.80 (2H, m), 1.30 (1H, m), 1.70 (2H, m), 2.20 (1H, m), 2.30 (1H, m), 2.65 (2H, m), 2.85 (1H, m), 3.15 (3H, br m), 3.50 (2H, m), 4.17 (1H, br d), 5.20 (1H, s), 6.80 (1H, d, J=8 Hz), 6.85 (1H, d, J=8 Hz), 7.18 (1H, s), 9.20 (1H, brs), and 9.70 (1H, s). $^{13}$C NMR ($d_6$-DMSO δ/ppm): 2.72, 5.24, 5.81, 22.98, 27.18, 30.73, 35.16, 46.11, 48.66, 56.73, 60.82, 69.83, 88.64, 118.09, 119.83, 120.59, 127.89, 140.22, 143.54, and 207.94. HPLC and IR spectra were consistent against a Naltrexone reference standard.

Example 3

Preparation of Naltrexone Hydrochloride from Nor-14-Hydroxymorphinone

Nor-14-hydroxymorphinone (20.0 g, equivalent to 62.1 mmol dry), cyclopropane carboxaldehyde (5.3 ml, 70.9 mmol), N-methylpyrrolidinone (60 in) and methanol (140 ml) were hydrogenated at 50° C. and 40 psi for 2 hours in the presence of palladium and platinum on carbon catalysts. The crude mixture was filtered, diluted with chloroform (60 ml), and then washed with water (200 ml). The aqueous phase was extracted with chloroform (2×60 ml) and the combined organic layer washed with water (5×140 ml). The chloroform was removed under reduced pressure and the resulting solid redissolved in ethanol (100 ml). The pH was lowered to <4.0 with hydrochloric acid and the precipitate filtered, washed with ethanol (10 ml) and dried to recover 19.2 g (83% theory) of a white solid corresponding with naltrexone hydrochloride by HPLC analysis.

Example 4

Preparation of Nalbuphine from Noroxymorphone

Cyclobutane carbonyl chloride (1.44 ml, 25.2 mmol) was hydrogenated for 2 hours in N-methylpyrrolidinone (30 ml) at 40 psi and room temperature in the presence of palladium on charcoal catalyst. The crude solution of cyclobutane carboxaldehyde was filtered through a bed of celite. To 15 ml of the above filtered solution, noroxymorphone (2.78 g, 7.96 mmol) was added followed by platinum on carbon catalyst and the mixture hydrogenated at 50° C. and 40 psi. After 2 hours the catalyst was filtered off and sodium borohydride (3 g) added portionwise. HPLC analysis of the crude reaction mixture and comparison against a known sample of nalbuphine confirmed the formation of nalbuphine.

Example 5

Preparation of Diprenorphine from Nordiprenorphine

Nordiprenorphine (2.0 g) was added to a solution of cyclopropanecarboxaldehyde (0.57 g) in methanol (16 ml) and N-methylpyrrolidinone (5 ml). Platinum on carbon catalyst added and mixture hydrogenated at 50° C. and 40 psi. After 30 minutes, the catalyst was filtered off and the reaction liquors diluted with chloroform (6 ml) and washed with water (20 ml). The product was extracted from the aqueous phase with chloroform (3×6 ml) and the combined organic layer washed with water (5×20 ml). The solvent was removed under vacuum to yield an off-white solid. HPLC analysis of the residue confirmed that the product was consistent with a reference standard of diprenorphine alkaloid.

Example 6

Preparation of Buprenorphine from Norbuprenorphine

Norbuprenorphine (10.0 g, 24.2 mmol), cyclopropanecarboxaldehyde (2.2 ml, 29.0 mmol), N-methylpyrrolidinone (30 ml) and methanol (70 ml) were hydrogenated at 50° C. and 40 psi for 2 hours in the presence of platinum on carbon catalysts. Upon completion, the catalyst was filtered off and water (200 ml) added. The product was extracted into chloroform (3×60 ml) and washed with water (5×140 ml). Chloroform was removed under vacuum and the residue redissolved in ethanol (50 ml). The pH was adjusted to <3.0 with hydrochloric acid. The product was filtered, washed with ethanol (5 ml) and dried in oven to yield 7.2 g of a white crystalline solid. HPLC analysis confirms the material is consistent with buprenorphine hydrochloride.

The invention claimed is:

1. A process for preparing a compound of formula (1):

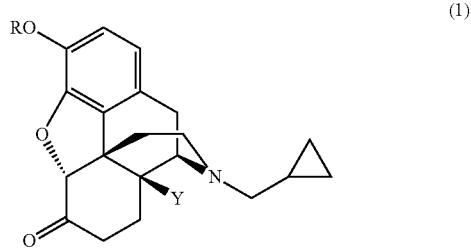

comprising reacting a compound of formula (D):

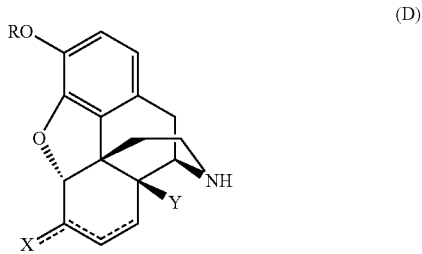

is no bond or a single bond with a compound of formula (G):

in the presence of hydrogen and a reductive alkylation catalyst in a solvent comprising an amine or amide;
wherein R is H or a hydroxyl protecting group;
X is O, a protected ketone, OH, or a protected hydroxyl group;
Y is OH or a protected hydroxyl group; and
Z is cyclopropyl.

2. The process according to claim 1, wherein R is H.
3. The process according to claim 1, wherein X is O or OH.
4. The process according to claim 1, wherein Y is OH.

5. The process according to claim 1, wherein R is H, X is O, and Y is OH.

6. The process according to claim 1, wherein the solvent comprises said amide and the amide is N-methylpyrrolidinone.

7. The process according to claim 6, wherein the solvent further comprises methanol.

8. The process according to claim 7, wherein the solvent is a 70:30 mixture of N-methylpyrrolidinone and methanol.

9. The process according to claim 1, wherein the solvent comprises said amide.

10. The process according to claim 1, wherein the compound of formula (D) is noroxymorphone and the compound of formula (1) is naltrexone.

11. The process according to claim 1, wherein the reductive alkylation catalyst is selected from the group consisting of platinum group metal catalysts, nickel catalysts, and mixtures of these.

12. The process according to claim 1, wherein the reductive alkylation catalyst comprises palladium on carbon.

13. The process according to claim 1, wherein the reductive alkylation catalyst comprises platinum on carbon.

14. The process according to claim 1, wherein the reductive alkylation catalyst comprises palladium and platinum on carbon.

* * * * *

UNITED STATES PATENT AND TRADEMARK OFFICE
CERTIFICATE OF CORRECTION

PATENT NO. : 8,119,803 B2  
APPLICATION NO. : 11/628210  
DATED : February 21, 2012  
INVENTOR(S) : Melville Mitchell et al.

Page 1 of 1

It is certified that error appears in the above-identified patent and that said Letters Patent is hereby corrected as shown below:

At column 7, line 8, "(60 in)" should read --(60 ml)--.

At column 8, line 46,

"is no bond or a single bond with a compound of formula (G):"

should read

--wherein.....is no bond or a single bond with a compound of formula (G):--.

At column 9, line 9,

"70:30 mixture of N-methylpyrrolidinone and methanol"

should read

--30:70 mixture of N-methylpyrrolidinone and methanol--.

Signed and Sealed this
Twenty-fifth Day of September, 2012

David J. Kappos
*Director of the United States Patent and Trademark Office*